(12) United States Patent
Song (10) Patent No.: US 7,968,517 B2
(45) Date of Patent: Jun. 28, 2011

(54) METHOD FOR TREATING WITHDRAWAL SYMPTOMS DUE TO OPIATE CONSUMPTION

(75) Inventor: Xue-Jun Song, Irving, TX (US)

(73) Assignee: Parker College of Chiropractic, Dallas, TX (US)

(*) Notice: Subject to any disclaimer, the term of this patent is extended or adjusted under 35 U.S.C. 154(b) by 0 days.

(21) Appl. No.: 12/290,566

(22) Filed: Oct. 31, 2008

(65) Prior Publication Data

US 2010/0111972 A1    May 6, 2010

(51) Int. Cl.
*A01N 37/18* (2006.01)
*A61K 38/00* (2006.01)
(52) U.S. Cl. .............. 514/18.3; 514/17.7; 514/18.2; 514/18.4
(58) Field of Classification Search .................. None
See application file for complete search history.

(56) References Cited

FOREIGN PATENT DOCUMENTS
WO    WO 2004/005345 A1 *    1/2004

OTHER PUBLICATIONS

Liu, et al., "EphB receptor signaling in mouse spinal cord contributes to physical dependence on morphine," *The FASEB Journal*, 23:1-10 (2009).
Han et al., "Targeted mutation of EphB1 receptor prevents development of neuropathic hyperalgesia and physical dependence on morphne in mice," *Molecular Pain*, 4(60):1-12 (2008).
Liu et al., "EphB receptor signaling in mouse spinal cord contributes to physical dependence on morphine," *Society for Neuroscience Annual Conference*, Presentation Abstract (Nov. 2008).
Liu et al., "Activation of ephrinB-EphB receptor signaling modulates behavioral signs of opioid withdrawal," *Society for Neuroscience Annual Conference*, Presentation Abstract (Nov. 2007).
Liu et al., "Spinal matrix metalloproteinase-9 contributes to physical dependence on morphine in mice," *J. of Neuroscience*, 30(22):7613-7623, 2010.

* cited by examiner

*Primary Examiner* — Olga N Chernyshev
(74) *Attorney, Agent, or Firm* — SNR Denton US LLP (57) ABSTRACT

The present invention provides a method for preventing or treating opiate tolerance and dependence by administering to an individual in need of such treatment with a pharmaceutically effective amount of a blocking reagent for ephrinB-EphB signaling. The opiate tolerance and dependence can be caused by chronic morphine treatment and withdrawal. The blocking reagent can be an EphB receptor blocker such as EphB1-Fc and EphB2-Fc.

5 Claims, 5 Drawing Sheets
(3 of 5 Drawing Sheet(s) Filed in Color)

METHOD FOR TREATING WITHDRAWAL SYMPTOMS DUE TO OPIATE CONSUMPTION

BACKGROUND OF THE INVENTION

1. Field of the Invention

The present invention generally relates to medical treatment. Particularly, the present invention relates to a method for preventing or treating the development of opiate tolerance and dependence using a blocking reagent for ephrinB-EphB signaling.

2. Description of the Related Art

Opioid drugs are used and abused for their analgesic and rewarding properties. Repeated use of opioids such as morphine for relief of chronic pain can lead to opiate tolerance and dependence. Mechanisms of opiate tolerance are very complex and involve factors at the levels of the drug receptor, the cell, and neural networks. Roles of diverse neurotransmitter and receptor systems and intracellular signaling proteins in acute and chronic opioid actions have been demonstrated (Bailey & Connor, 2005; Bohn et al, 2000; Collier, 1980; King et al, 2001; Muscoli et al, 2007; Pasternak, 2007; Roerig et al, 1984; Zachariou et al, 2003). The most intensively studied system is the glutamate/NMDA receptor/NO cascade (Ben-Eliyahu et al, 1992; Inoue et al, 2003; Inturrisi, 2002; Kolesnikov et al, 1998; Kolesnikov et al, 1993; Kolesnikov et al, 1992; Muscoli et al, 2007; Pasternak, 2007; Pasternak & Kolesnikov, 2005; Trujillo & Akil, 1991). Adaptive changes following chronic opioid exposure that might underlie physical dependence by altering neuronal excitability and synaptic transmission include a withdrawal-induced rebound increase in cAMP levels and in expression of the cAMP response element binding protein (CREB) (Barrot et al, 2002; Nestler, 2001; Shaw-Lutchman et al, 2002) and MAPKs (Sweatt, 2004). The capacity of agonists to recruit various μ-opioid receptor (MOR) regulatory events has recently been suggested to be a major determinant of their propensity to induce both tolerance and dependence (Bailey & Connor, 2005). Despite decades of investigation, the specific cellular and molecular mechanisms underlying opioid tolerance and withdrawal-induced pain enhancement remain elusive. One general possibility is that repetitive or prolonged MOR activation may elicit neuronal alterations that recapitulate events during development (Chen et al, 2007) including the promotion of synapse formation. It is of clinical important to determine the mechanisms underlying tolerance and physical dependence, and to develop medications that can prevent, minimize, or reverse opioid tolerance and dependence.

Eph-receptors constitute the largest subfamily of receptor tyrosine kinases (RTKs), and they play vital roles in transmitting external signals to the inside of many types of cells. In humans there are 13 Eph-receptor genes, divided into an A-subclass (EphA1-EphA8) and a B-subclass (EphB1-EphB4, EphB6). Their ligands, the ephrins, are also divided into two subclasses: ephrinA1-ephrinA5 and ephrinB1-ephrinB3. A-type receptors typically bind to most or all A-type ligands, and B-type receptors bind to most or all B-type ligands (Kullander & Klein, 2002). Eph RTKs and ephrins are involved in tissue-border formation, cell migration, and axon guidance during development of the nervous system (Krull et al, 1997; Wang & Anderson, 1997; Wilkinson, 2000; Wilkinson, 2001). EphB receptors can also regulate the development and remodeling of glutamatergic synaptic connections and their plasticity in adult nervous system by interaction with NMDA receptors (NMDARs) (Chen et al, 2007; Dalva et al, 2000; Grunwald et al, 2004; Grunwald et al, 2001; Henderson et al, 2001; Takasu et al, 2002). NMDARs containing both NR1 and NR2 subunits have an established role in neural plasticity and are fundamental mediators of expression, development and maintenance of opiate tolerance, dependence and withdrawal (Bailey & Connor, 2005; Herman et al, 1995; Mao, 1999; Mao et al, 2002; Mayer et al, 1999; Noda & Nabeshima, 2004; Zhu & Barr, 2001). The opiate systems interact with NMDARs such that MOR activation results in $Ca^{2+}$ influx through the NMDAR ion-channel complex. The subsequent activation of various $Ca^{2+}$-dependent enzymes, such as $Ca^{2+}$/calmodulin-dependent kinase (CaMK) (Fan et al, 1999; Hamdy et al, 2004; Liang et al, 2004; Lou et al, 1999; Lu et al, 2000) and ERK (Ren et al, 2004; Schulz & Hollt, 1998) play a central role in the induction of persistent opioid effects (Noda & Nabeshima, 2004).

Recent studies have further demonstrated that peripheral inflammation and/or nerve injury enhances ephrinB-EphB receptor signaling (Kobayashi et al, 2007; Song et al, 2008a), and such signaling may contribute to inflammatory and neuropathic pain by altering neural excitability and synaptic transmission via interaction with NMDARs in the spinal cord (SC) (Battaglia et al, 2003; Song et al, 2008a; Song et al, 2008b). Several lines of evidence indicate that the spinal dorsal horn (DH), the first central relay station for processing nociceptive information, is an important site in the development of opioid dependence and withdrawal (Jhamandas et al, 1996; Mao et al, 2002; Marshall & Buccafusco, 1985; Mayer et al, 1999; Muscoli et al, 2007; Rohde & Basbaum, 1998; Rohde et al, 1996; Rohde et al, 1997; Trang et al, 2003).

There is apparently a need for an effective method for preventing, minimizing or reversing opiate tolerance and dependence. The present invention fulfills this long-standing need.

SUMMARY OF THE INVENTION

The present invention demonstrates contribution of EphB receptor signaling to the development and maintenance of physical dependence on opioid drugs and to characteristic responses after withdrawal of such drugs. The present invention further provides methods for preventing or treating opiate tolerance and dependence.

In detail, the present invention is directed to a method for preventing or treating opiate tolerance and dependence by administering to an individual in need of such treatment with a pharmaceutically effective amount of a blocking reagent for ephrinB-EphB signaling. The opiate tolerance and dependence is preferably caused by chronic morphine treatment and withdrawal.

The foregoing and other advantages of the present invention will be apparent to those skilled in the art, in view of the following detailed description of the preferred embodiment of the present invention, taken in conjunction with the accompanying drawings.

BRIEF DESCRIPTION OF THE DRAWINGS

The present application file contains at least one drawing executed in color. Copies of this patent application publication with color drawing(s) will be provided by the Office upon request and payment of the necessary fee.

Features of the present invention as well as a preferred mode of use, further objectives, and advantages thereof, will best be understood by reference to the following detailed description of an illustrative embodiment when read in conjunction with the accompanying drawing, wherein:

FIGS. 1A-1D illustrate attenuation of morphine withdrawal by EphB2-Fc in accordance with the present invention.

FIGS. 4A-4G illustrate altered expression of EphB1 receptor and ephrinB protein in the spinal cord (SC) following escalating morphine treatment, morphine withdrawal and spinal administration of EphB2-Fc in accordance with the present invention. Examples and data summary of the expression of EphB1 receptor protein following escalating morphine exposure or escalating morphine exposure combined with repeated pulses of EphB receptor blocker are shown in FIG. 4A and FIG. 4B, respectively.

FIGS. 5A-5D illustrate effects of EphB2-Fc on increases of the phosphorylated NR2B, ERK and CREB in SC following morphine treatment and withdrawal in accordance with the present invention. FIGS. 5B and 5D demonstrate data summary. *, $p<0.05$, **, $p<0.01$ indicate significant differences compared with the corresponding Naïve group. #, $p<0.05$, ##, $p<0.01$ indicate significant difference compared with the corresponding morphine (Mor) group.

DETAILED DESCRIPTION

The present invention demonstrates contribution of EphB receptor signaling to the development and maintenance of physical dependence on opioid drugs and to characteristic responses after withdrawal of such drugs. The present invention further provides methods for preventing or treating opiate tolerance and dependence.

Eph receptor tyrosine kinases and their ephrin ligands play an important role in neural synaptic plasticity. It has recently been reported that activation of ephrinB-EphB receptor signaling is critical for development of neuropathic pain. The present study investigated if ephrinB-EphB receptor signaling would also be involved in modulation of behavioral and neurochemical manifestations of opioid withdrawal. The results show that intrathecal treatment (i.t.) of EphB receptor antagonists EphB2-Fc (2 μg post the last dose of morphine) significantly suppressed the withdrawal syndromes. The control injection of PBS and human Fc did not produce significant effects on the withdrawal syndromes. Furthermore, repetitive treatment of EphB2-Fc at lower doses (1 μg, i.t., 7 doses along with the seven doses of morphine) significantly suppressed the withdrawal syndromes, and such inhibition was significantly greater than that produced by the single treatment at a higher dose. The results also show that naloxone challenge significantly increased the number of Fos-like immunoreactive neurons in the dorsal horn and that EphB2-Fc treatment significantly reduced the c-Fos expression. These studies suggest that activation of ephrinB-EphB receptor signaling may contribute to the expression of opioid physical dependence in the spinal cord and that blockage of EphB receptors could be effective in diminishing the physical signs of withdrawal.

The present invention is directed to a method for preventing or treating opiate tolerance and dependence by administering to an individual in need of such treatment with a pharmaceutically effective amount of a blocking reagent for ephrinB-EphB signaling.

In a preferred embodiment, the opiate tolerance and dependence is caused by chronic morphine treatment and withdrawal.

The blocking reagent can be an EphB receptor blocker, two examples of which are EphB1-Fc and EphB2-Fc. The blocking reagent can be administrated intrathecally to the individual in need of such treatment in the dosage range of from about 0.5 μg to about 75 mg, preferably, from about 1 μg to about 15 mg. The blocking reagent can be either co-administrated with morphine repeatedly or administered in a single dose post morphine administration. The individual being treated is usually a mammal, preferably, a human.

The following example is given for the purpose of illustrating various embodiments of the invention and is not meant to limit the present invention in any fashion.

EXAMPLES

Materials and Methods

Animals

Male CD-1 mice (25-30 g, n=237, Charles River Laboratories, MA) were used in this study. The mice were housed in plastic cages with soft bedding and free access to food and water under a 12 h day/12 h night cycle. All the experimental procedures were conducted in accordance with the regulations of the ethics committee of the International Association for the Study of Pain and approved by the Parker Research Institute Animal Care and Use Committee.

Opiate Withdrawal

Mice were injected i.p. with repeated pulses of morphine (Sigma, MO) given in 7 escalating doses every 8 h (20, 40, 60, 80, 100, 100, and 100 mg/kg). Two hours after the last morphine injection, mice were injected with naloxone (Sigma, MO) (1 mg/kg, s.c.), and withdrawal symptoms (jumping, wet-dog shakes, backward walking, paw tremor, tremor, diarrhea, ptosis, and weight loss) were monitored for 30 min after naloxone administration. In addition to measuring individual withdrawal signs, an overall opiate withdrawal score was calculated as (no. of backward walking steps×0.1)+(diarrhea×2)+(no. of jumps×0.1)+(paw tremor×0.1)+(ptosis)+(tremor)+(% weight loss×5)+(no. of wet-dog shakes) (Zachariou et al, 2003). Contributions of ephrinB-EphB signaling to spinal mechanisms of morphine dependence and withdrawal were investigated by applying the EphB receptor blocking reagents EphB2-Fc (this molecule binds to ephrinB1-3; mouse recombinant; Sigma, E9402) to the SC in vivo. Intrathecal administration (i.t.) was performed by means of lumbar puncture with a 25 ml Halmiton syringe with a 30 gauge needle as previously described (Hylden & Wilcox, 1980). EphB2-Fc was delivered in either 7 pulses (1 µg each) accompanying the 7 escalating morphine doses or 1 pulse (2 µg) 30 min before naloxone. The IgG-Fc fragment (Jackson, Fc control, 1 µg each dose) and vehicle PBS (1 pulse for each morphine dose) were administered as control. All were in a volume of 5 µl.

Pain Threshold and Morphine Analgesia Tests

To test possible effects of EphB2-Fc and IgG-Fc on the pain threshold and the initial analgesic response to morphine, mice were placed on a 55° C. hot plate apparatus, and the latency to lick a paw was measured. A cutoff time of 30 s was set to avoid tissue damage. Mice were tested every 30 min for 2 or 2.5 h. Data were calculated as percent maximal possible effect (% MPE), which was calculated by the following formula: 100%×[(drug response time−basal response time)/(30 sec−basal response time)]=% MPE. Morphine was administered (10 mg/kg, s.c.) 30 min before testing. EphB2-Fc and IgG-Fc (2 µg, i.t.) were administered at time 0 in FIG. 1C and together with morphine in FIG. 1D.

Immunohistochemical and Immunofluorescence Staining of c-Fos, CGRP and EphB1 Receptor Mice were anesthetized and perfused transcardially with cold saline followed by ice-cold 4% paraformaldehyde solution. The lumbar segment of the SC was dissected out and post-fixed at 4° C. for 4 h with the paraformaldehyde solution, then the Histo Prep (Fisher Scientific, Fair Lawn, N.J.) embedded blocks were sectioned on a Leica CM1850 cryostat (Leica Microsystems, Germany). Sections (10 µm) were thaw-mounted on to glass slides and allowed to air dry. The immunofluorescence staining was performed as previously described (Kerr et al, 2000). Endogenous peroxidases were blocked by incubating tissue sections with 0.3% hydrogen peroxide for 30 min and 3% normal goat serum for 20 min. Sections were washed three times in PBS between incubation. Sections from each group (5 mice in each group) were then incubated with rabbit anti-c-Fos polyclonal antibody (1:100) and rabbit anti-EphB1 polyclonal antibody (1:200), (both from Santa Cruz Biotechnology Inc. Santa Cruz, Calif.), rabbit anti-CGRP polyclonal antibody (1:1000, Millipore, Billerica, Mass.) respectively. Rabbit IgG was used as an isotype control. After overnight incubation with primary antibody at 4° C., tissue sections were washed and incubated in a dark, high humidity chamber at room temperature with fluorescent labeled goat anti rabbit IgG (1:200, Vector Laboratories, Inc., Burlingame, Calif.) for 1 h. After washing with PBS, the slides were mounted using Vectashield H-1400 mounting medium (Vector Laboratories, Inc., Burlingame, Calif.).

The morphologic details of the immunofluorescence staining on SC were studied under a fluorescence microscope (Olympus BX51WI; Olympus America Inc., Melville, N.Y.). Images were randomly coded and transferred to a computer for further analysis. Fos-immunoreactive neurons were counted in blind fashion. The number of Fos-like immunoreactive neurons in DH (laminae I-VI) was determined by averaging the counts made in 20 SC sections (L4-L5) for each group. To obtain quantitative measurements of CGRP immunofluorescence, 15-20 fields covering the entire DH in each group were evaluated and photographed at the same exposure time to generate the raw data. Fluorescence intensities of the different groups were analyzed using MicroSuite image analysis software (Olympus America Inc.). The average green fluorescence intensity of each pixel was normalized to the background intensity in the same image Western Blot Analysis Western blot analysis was used to detect expression of EphB receptors, ephrinBs, and phosphorylated NR2B, ERK and CREB proteins in the SC. A total of 108 mice were used for Western blotting experiments (SC from 4 mice were pooled for each sample and each group consisted of 3 samples). The lumbar segments of the SC were quickly extracted and immediately frozen in liquid nitrogen, and stored at −80° C. The procedure used to quantify temporal changes in protein levels was similar to that previously described (Bundesen et al, 2003). In brief, protein precipitation procedures in conjunction with Western blots were used to detect protein bands with an enhanced chemiluminescent (ECL) detection procedure. Sequential precipitation procedures were used on tissue samples that were lysed in ice-cold (4° C.) lysis buffer [50 mM Tris, pH 7.5, containing 150 mM NaCl, 1% Triton X-100, 0.5% deoxycholate, 0.1% SDS, 0.2 mM EDTA, 10 mM NaF, 10 g/ml aprotinin, 1 g/ml leupeptin, 10 g/ml pepstatin, 0.4 mM 4-(2-aminoethyl)-benzenesulfonyl fluoride, and 1 mM sodium orthovanadate. The protein concentration of the lysates was estimated using the method of BCA (Pierce, Ill.), and the total protein content between samples was equalized. Initially, EphB1 was immunoprecipitated from 2 mg total protein/ml tissue lysate using an anti-EphB1 antibody (2 µg, Q-20, Santa Cruz, Calif.), while ephrinBs were immunoprecipitated from 2 mg total protein/ml tissue lysate using the Protein G-Agarose (Invitrogen) linked to agarose (50 µl of 50% slurry; 5 mg/ml binding capacity; Sigma), respectively. After overnight incubation, the precipitated protein complexes were washed in three changes of cold (4° C.) lysis buffer. EphB1 and ephrin-B proteins were dissociated by heating at 100° C. for 5 min in sample buffer (2% SDS, 100 mM DTT, 10% glycerol, and 0.02% bromophenol blue) before loading on 8 or 10% SDS polyacrylamide gels to resolve protein bands. For the p-NR2B, p-CREB, p-ERK, GAPDH Western blot analysis, whole cell protein extracts lysates were used. After transfer to nitrocellulose filters, the filters were blocked with 2% bovine serum albumin (BSA) and then incubated overnight at 4° C. with the primary antibodies (EphB1 1:100, Q20, ephrinB1 1:100, H70, ephrinB2 1:100, C20, PY99 1:100, and p-CREB (Ser133) from Santa Cruz, Calif.; p-NR2B (Tyr 1472) 1:300 from Chemicon, CA; p-ERK½ (Thr202/Tyr204) 1:500 from Cell Signaling Technology, MA; GAPDH 1:1000 from Sigma, MO). The filters were developed using ECL reagents (Perkinelmer, MA) with secondary antibodies from Chemicon. Data were analyzed with the Molecular Imager (Gel Doc™ XR, 170-8170) and the associated software Quantity One-4.6.5 (Bio-Rad Laboratories, Hercules, Calif.).

Statistical Tests

Change of expression of the proteins detected and differences in latency over time among groups were tested with one-way ANOVA and two-way ANOVA, respectively, with repeated measures followed by Bonferroni post hoc tests. Individual t-tests were used to test specific hypotheses about differences between each test group and its corresponding control group. All data are presented as mean±SEM. Statistical results are considered significant if $p<0.05$.

Results

Figure 1A:
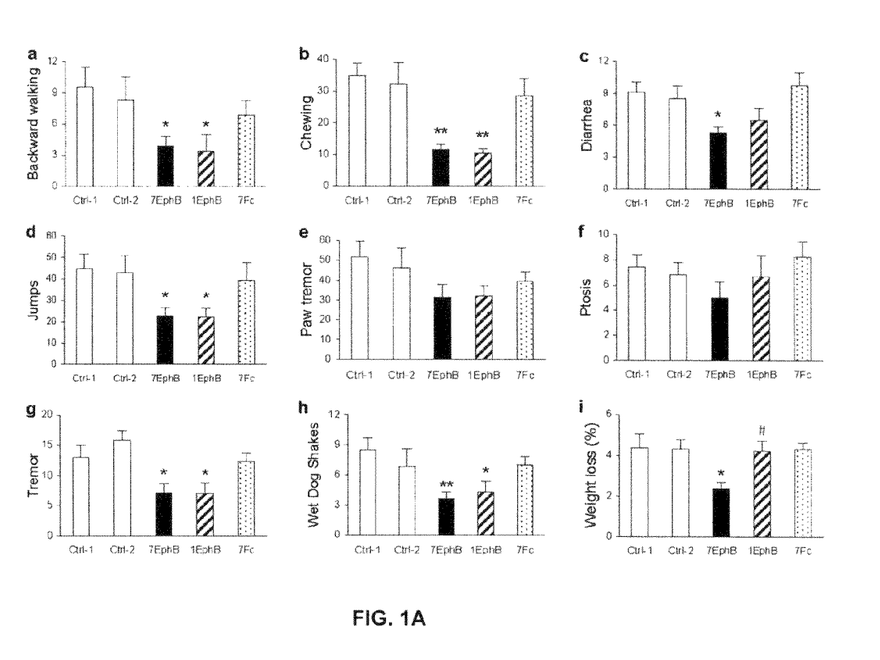
FIG. 1A illustrates effects of EphB2-Fc on the behavioral signs of naloxone-precipitated morphine withdrawal. In addition to receiving morphine and naloxone, the different groups received one of the following treatments (i.t.): control one (Ctrl-1)—no additional treatment; control two (Ctrl-2)—PBS; 7EphB, seven pulses of EphB2-Fc accompanied morphine; 1EphB, one pulse of EphB2-Fc (2 μg, 5 min after the last morphine); 7Fc, seven pulses of IgG-Fc (1 μg accompanied morphine).
Figure 1B:
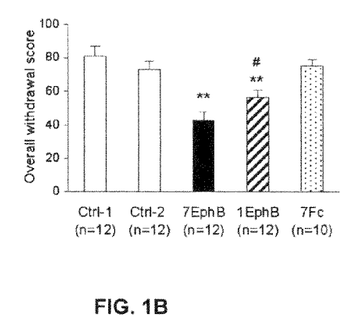
FIG. 1B illustrates overall withdrawal scores of each group.
Figure 1C:
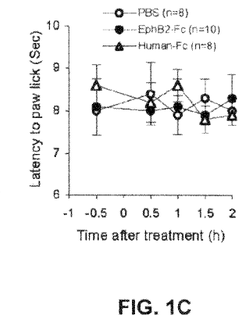
FIG. 1C illustrates effects of EphB2-Fc (2 μg) and IgG-Fc (2 μg) on the pain threshold in naïve mice.
Figure 1D:
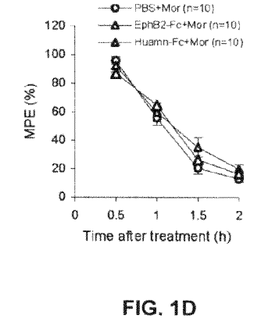
FIG. 1D illustrates effects of EphB2-Fc (2 μg) and IgG-Fc (2 μg) on the initial analgesic response to morphine. Mor represents morphine. *, $p<0.05$, **, $p<0.01$ indicate significant differences compared with Cntrl-1. #, $p<0.05$ indicate significant difference between 1EphB and 7EphB groups.

EphB Receptor Blocker Prevents and Suppresses Behavioral Signs of Naloxone-Precipitated Morphine Withdrawal Naloxone-participated morphine withdrawal results in a characteristic morbidity, including anxiety, nausea, insomnia, hot and cold flashes, muscle aches, perspiration and diarrhea. Intrathecal injection (i.t.) of a reagent that can block activation of EphB receptors, the chimeric molecule EphB2-Fc, significantly attenuated most of the morphine withdrawal signs and overall withdrawal score in mice. As shown in FIG. 1A(a)-(i), repeated co-application of EphB2-Fc (1 µg during each of the 7 morphine doses) significantly attenuated the backward walking, chewing, diarrhea, jump, tremor, wet dog shake and weight loss, but not the paw tremor and ptosis accompanying withdrawal. Following the morphine applications, a single treatment of EphB2-Fc at a larger dose (2 µg, 30 min prior to naloxone) also significantly attenuated the withdrawal symptoms, backward walking, chewing, jump, tremor, and wet dog shake, but not diarrhea, paw tremor, ptosis or weight loss. Consistent with these changes, the overall withdrawal score was significantly reduced in EphB2-Fc treated mice (FIG. 1B). Repeated co-application of EphB2-Fc produced greater inhibition than the single, post-morphine application of the blocker on the overall withdrawal score (FIG. 1B). Human IgG Fc (IgG-Fc, 2 µg, i.t.) did not significantly affect the withdrawal behaviors (FIGS. 1A and 1B). Neither EphB2-Fc (2 µg, i.t.) nor IgG-Fc (2 µg, i.t.) altered the pain threshold (FIG. 1C) or the initial morphine-induced analgesia (FIG. 1D). PBS was used as control in both FIGS. 1C and 1D. These results indicate that blocking the activation of EphB receptors can attenuate morphine withdrawal symptoms, suggesting that the EphB receptors may be involved in spinal mechanisms of opiate dependence and withdrawal.

Figure 2A:
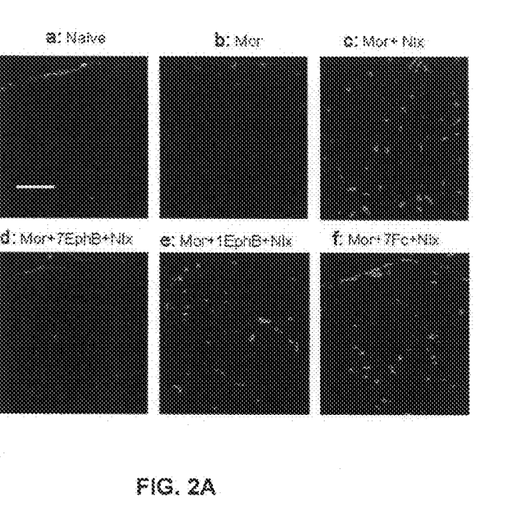
FIGS. 2A-2B illustrate reduction of c-Fos expression by EphB2-Fc in the dorsal horn (DH) during morphine withdrawal in accordance with the present invention. Examples of Fos-immunoreactive neurons are given in FIG. 2A and data summarized in FIG. 2B. **, $p<0.01$ indicate significant differences compared with naïve. #, $n<0.05$, ##, $p<0.01$ indicate significant difference compared with Mor+Nlx. $^{\&}p<0.05$ indicates significant difference between groups of Mor+7EphB+Nlx and Mor+1EphB+Nlx. Scale bars: 200 μm.
Figure 2B:
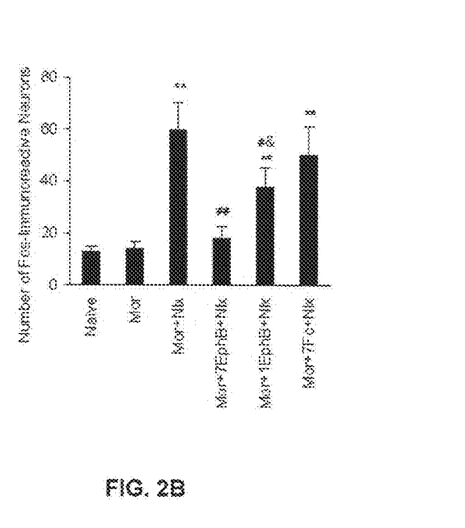

EphB Receptor Blocker Suppresses the Induction of c-Fos and Accumulation and Depletion of CGRP in the DH Following Morphine Treatment and Withdrawal Induction of c-Fos protein expression following opiate withdrawal, and the increase and then decrease in CGRP expression in the DH following chronic morphine exposure and during withdrawal have been used as indicators of neural activity and plasticity associated with these states (Chieng et al, 1995; Jhamandas et al, 1998; Rohde et al, 1996; Rohde et al, 1997; Trang et al, 2006; Trang et al, 2002; Trang et al, 2003). Immunohistochemical and immunofluorescence staining were used to measure the expression of c-Fos and CGRP-immunoreactivity. Six groups of mice (n=5 each group) were tested and examined: Naïve (Aa) received no treatment; Mor (Ab) received escalating morphine treatment; Mor+Nlx (Ac) received naloxone after the morphine treatment; Ad-Af, in addition to receiving the morphine and naloxone, received seven pulses of EphB2-Fc (1 µg) (Mor+7EphB+Nlx) (Ad); one treatment of EphB2-Fc (2 µg) 30 min prior to naloxone (Mor+1EphB+Nlx) (Ae); and repeated pulses of IgG-Fc (1 µg) (Mor+7Fc+Nlx)(Af). Representative photomicrographs and the corresponding counts of Fos-like immunoreactive neurons in DH are shown in FIG. 2A and FIG. 2B, respectively. As expected, c-Fos expression significantly increased during morphine withdrawal (FIG. 2Aa-c). Interestingly, EphB2-Fc, i.t., prevented or significantly suppressed the increase in expression of c-Fos. Repeated application of EphB2-Fc (1 µg, 7 times at 8 h intervals, accompanied by morphine) completely prevented expression of c-Fos (FIG. 2Ad), while single dose of EphB2-Fc (2 µg, 30 min prior to naloxone challenge) significantly reduced the increase in expression of c-Fos (FIG. 2Ae). IgG-Fc (1 µg, i.t.) did not significantly affect the induction of c-Fos expression (FIG. 2Af). Data are summarized in FIG. 2B.

Figure 3A:
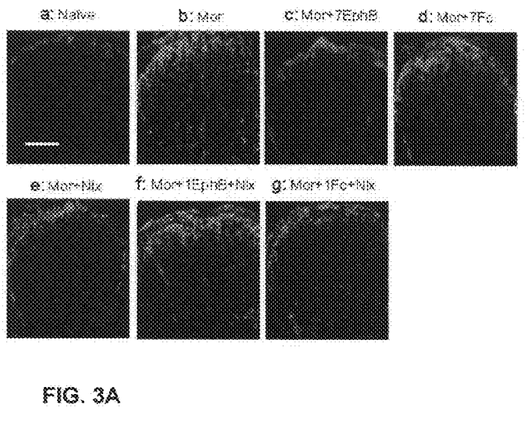
FIGS. 3A-3B illustrate reduction of the alterations in CGRP-immunoreactivity by EphB2-Fc in the DH associated with repeated, escalating morphine doses and morphine withdrawal in accordance with the present invention. **, $p<0.01$ indicate significant difference compared with group of Naïve. #, $p<0.05$, ##, $p<0.01$ indicate significant difference compared with group of morphine (Mor). $^{\&}p<0.01$ indicates significant difference between groups of Mor+Nlx and Mor+1EphB+Nlx. Scale bars: 200 μm.
Figure 3B:
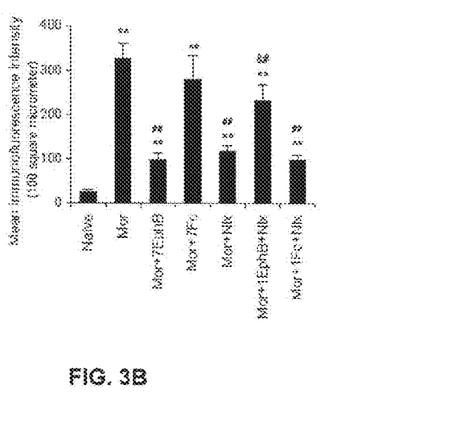

Alterations of CGRP-immunoreactivity in the DH associated with chronic morphine and morphine withdrawal and the given drug treatment are shown in FIG. 3. Six groups of mice (n=5 each group) were tested and examined: Naïve (Aa) received no treatment; Mor (Ab) received escalating morphine treatment; Mor+Nlx (Ac) received naloxone after morphine treatment; Mor+1EphB+Nlx (Ad) received one treatment of EphB2-Fc (2 µg) 30 min prior to naloxone in addition to Mor+Nlx; Mor+7Fc+Nlx (Ae) received repeated pulses of IgG-Fc (1 µg) in addition to Mor+Nlx; Mor+7EphB (Af) received morphine treatment with repeated pulses of EphB2-Fc (1 µg). As expected, repeated morphine exposure greatly increased the expression of CGRP throughout the DH region of the SC (FIG. 3A(a)-(b)). Repeated application of EphB2-Fc, but not the IgG-Fc (each administered 1 µg during each morphine dose) significantly prevented the chronic morphine-induced increase of CGRP-like immunoreactivity (FIG. 3A(c)-(d)). Morphine withdrawal resulted in markedly reduction of the CGRP immunoreactivity (FIG. 3Ae). A single application of EphB2-Fc, but not human Fc (each administrated 2 µg, i.t., 30 min prior to naloxone) significantly attenuated the withdrawal-associated reduction of CGRP immunoreactivity (FIG. 3A(f)-(g)). The corresponding measurements of fluorescence intensity are summarized in FIG. 3B.

Expression of EphB1 Receptor is Upregulated by Chronic Morphine Treatment and Morphine Withdrawal in SC Given that activation of EphB receptors is necessary for induction and/or maintenance of the behavioral and neurochemical signs associated with naloxone-precipitated morphine withdrawal, an interesting question is whether EphB receptors and their ligands are regulated/modulated by chronic morphine exposure and/or morphine withdrawal. Protein precipitation procedures were used in conjunction with Western blots (Bundesen et al, 2003) to detect expression of EphB receptors and ephrinB proteins.

Figure 4A:
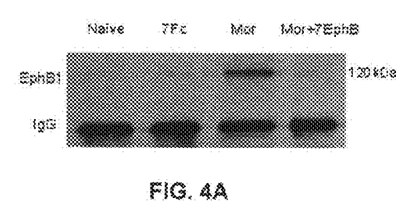
Figure 4B:
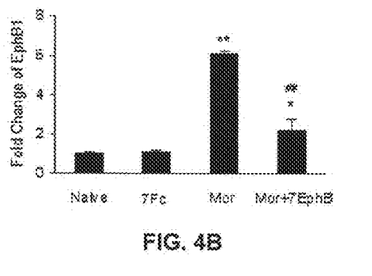
Figure 4C:
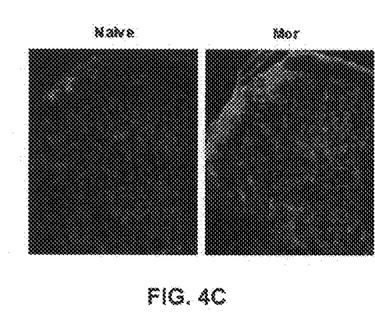
FIG. 4C illustrates Example of the distribution of EphB1 receptor protein in the DH indicated by immunofluorescence staining. Examples and data summary of EphB1 receptor protein expression 30 min after morphine withdrawal following escalating morphine treatment or morphine treatment combined with single or repeated pulses of EphB receptor blocker are shown in FIG. 4D and FIG. 4E, respectively.
Figure 4D:
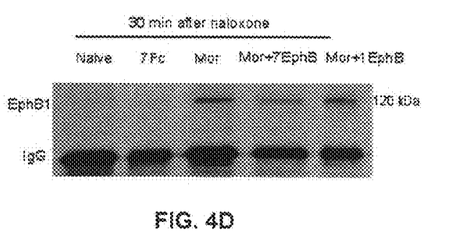
Figure 4E:
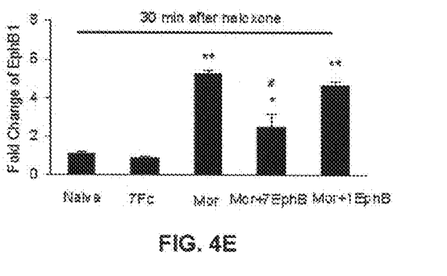
Figure 4F:
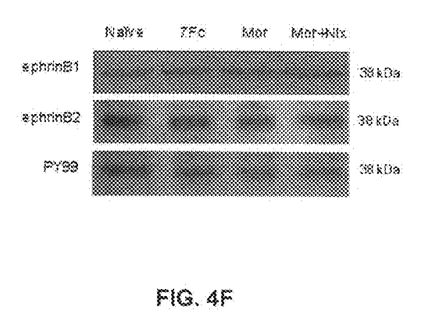
FIG. 4F and FIG. 4G illustrate effect of morphine treatment and morphine withdrawal on expression of ephrinB1, ephrinB2 and PY99. *, $p<0.05$, **, $p<0.01$ indicate significant difference compared with group of Naïve. #, $p<0.05$, ##, $p<0.01$ indicate significant differences compared with group of chronic morphine (Mor).
Figure 4G:
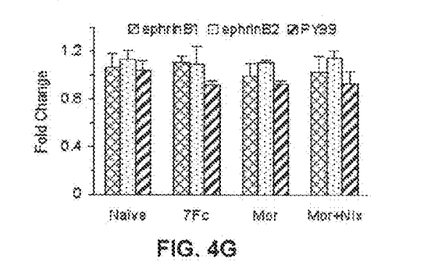

Each group consists of 3 samples and each sample includes 4 spinal lumbar segments from 4 mice. The Naïve group received no treatment, 7Fc received 7 repeated pulses of human Fc, Mor received escalating morphine treatment, Mor+7EphB received escalating morphine treatment with the EphB receptor blocker EphB2-Fc (1 µg, 7 pulses), and Mor+1EphB received escalating morphine treatment followed by a single pulse of EphB receptor blocker EphB2-Fc (2 µg). Expression of EphB1 receptor protein significantly increased after escalating morphine treatment (FIGS. 4A and 4B). Immunohistochemical fluorescence staining further showed that the increased expression of EphB1 receptor protein was predominantly localized to the superficial laminae of the DH (FIG. 4C). Most of the increased expression of EphB1 receptor protein was prevented or cancelled in the mice that received simultaneous treatment of escalating morphine doses and repeated pulses of the EphB receptor blocker EphB2-Fc (1 μg, i.t., 7 doses) (FIGS. 4A and 4B). Similar results were found after naloxone treatment (FIGS. 4D and 4E). Naloxone treatment did not significantly alter the morphine-induced increase in EphB1 receptor protein expression or the inhibition of EphB1 receptor protein expression caused by repeated pulses of EphB2-Fc. A single treatment of EphB2-Fc (2 μg, i.t., 30 min prior to naloxone) failed to significantly reduce the morphine-induced increase in EphB1 receptor protein expression (FIG. 4E). These results indicate that the EphB1 receptor is upregulated by the escalating morphine treatment and by morphine withdrawal, and inhibited by co-application of the receptor blocker, which also attenuated the behavioral symptoms and neurochemical signs of morphine withdrawal, although the results failed to show significant changes in expression of ephrinB1 or ephrinB2 or of phosphotyrosine (PY99) proteins following escalating morphine treatment or morphine withdrawal (FIGS. 4F and 4G).

EphB Receptor Blocker Prevents or Suppresses the Increase in Phosphorylated NR2B, ERK and CREB Associated with Chronic Morphine Treatment and Morphine Withdrawal NMDARs have a well-established role in opiate-related neural plasticity (Mao, 1999; Mayer et al, 1999; Zhu & Barr, 2001). Chronic morphine treatment causes increases in $Ca^{2+}$ levels and alterations of CaMKII (Liang et al, 2004; Lu et al, 2000), ERK (Ren et al, 2004; Schulz & Hollt, 1998) and CREB (Nestler, 2001). A question to be answered in the present study is whether these signals are modulated by the activity of EphB receptors after morphine treatment and withdrawal.

Figure 5A:
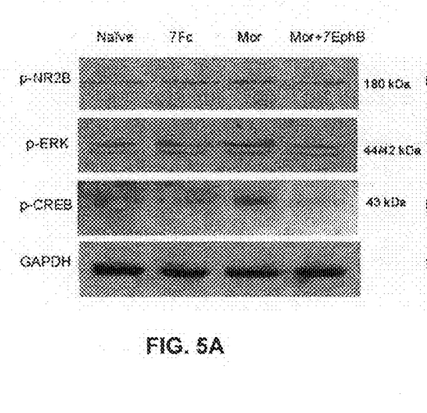
FIGS. 5A and 5C show examples of expression of the proteins tested after different treatments.
Figure 5B:
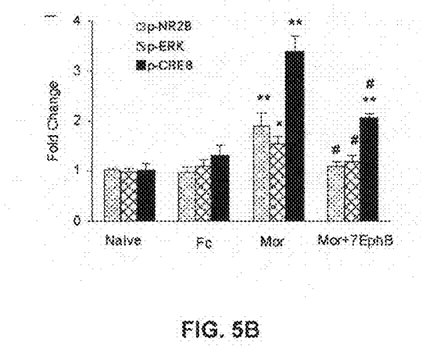
Figure 5C:
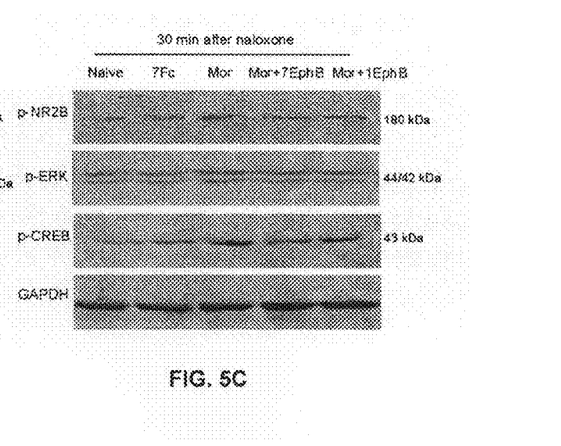
Figure 5D:
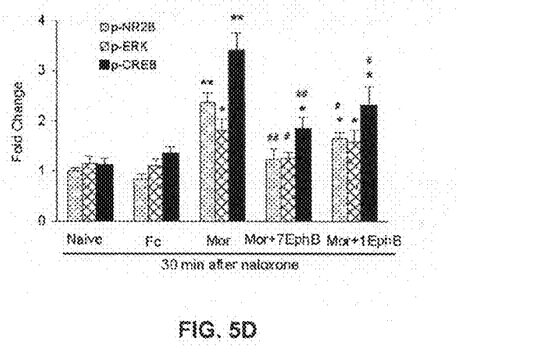

Different groups of mice received the same treatments as in FIGS. 4A and 4C. Data summary is shown in FIGS. 5B and 5D. The results illustrate that escalated morphine treatment caused significant increases in the levels of p-NR2B, p-ERK, or p-CREB protein, as indicated by Western blots (FIGS. 5A and 5B). Co-application of EphB2-Fc with morphine significantly prevented or reduced the morphine-induced increase in phosphorylated NR2B, ERK and CREB (FIG. 5B). Following morphine withdrawal (30 min after naloxone), there was no further increase in the p-NR2B, p-ERK, or p-CREB levels (FIGS. 5C and 5D). Repeated co-application of EphB2-Fc significantly attenuated the increased levels of each phosphorylated protein, while a single co-application of EphB2-Fc significantly inhibited the increases in p-NR2B and p-CREB, but not p-ERK (FIG. 5D). These data indicate that activity of EphB receptors can modulate the NMDARs and intracellular signals that are related to chronic morphine exposure and morphine withdrawal.

Discussion

The present study provides the first evidence that EphB receptor signaling in the SC contributes to the development of morphine dependence and withdrawal. The principal findings are 1) escalating morphine treatment significantly upregulates expression of EphB1 receptor protein in the SC; 2) intrathecal administration of a blocking reagent for EphB receptors prevents and/or suppresses the behavioral symptoms and neurochemical signs associated with chronic morphine treatment or morphine withdrawal, including induction of c-Fos, and accumulation and then depletion of CGRP in the DH, accompanied by recovery of EphB1 receptor protein expression; 3) levels of the p-NR2B subunit of NMDARs, as well as p-ERK and p-CREB in the SC are significantly increased following chronic morphine treatment and withdrawal; and these increases are prevented or reduced by co-application of an EphB receptor blocking reagent with morphine. These findings indicate that EphB receptor signaling in the SC may play an important role in opioid physical dependence, probably by interacting with the NR2B subunit of NMDARs.

The EphB receptors, in addition to their important roles in tissue-border formation, cell migration, and axon guidance during development of the nervous system, can regulate the development of glutamatergic synaptic connections and their plasticity in the adult nervous system by interaction with NMDA receptors (Chen et al, 2007; Dalva et al, 2000; Grunwald et al, 2004; Grunwald et al, 2001; Henderson et al, 2001; Takasu et al, 2002). The present study demonstrated that the EphB receptors may contribute to the development of morphine dependence and withdrawal by interacting with the NR2B subunit of NMDAR, thus regulating excitability and synaptic plasticity in DH neurons although whether EphB receptor-mediated stimulation of DH neurons occurs postsynaptically, presynaptically, or both pre-and postsynaptically and whether or not reverse signaling through activation of ephrinB also plays a role, either pre-or postsynaptically remains to be seen. The EphB receptors are membrane proteins that initiate bidirectional signaling when the proteins aggregate (Kullander & Klein, 2002; Palmer & Klein, 2003). However, the accumulation of EphB receptors in the DH and the inhibition of CGRP expression in primary afferent fibers within the DH by a blocking reagent of EphB receptors after morphine treatment suggest that EphB receptor signaling may be important on both sides of synapse, and that both forward and reverse ephrinB-EphB signaling in the SC may contribute to morphine dependence and withdrawal symptoms. Although the available blocking reagents do not identify the specific EphB receptors that re activated, the specificity of the antibodies used for detection of EphB1 lends confidence to the conclusion that these specific proteins are upregulated during chronic morphine exposure and withdrawal. In addition, recent unpublished data obtained from EphB1 knockout (KO) mice also indicate that the EphB1 receptor is important to the development of morphine dependence, i.e., behavioral signs of naloxone-precipitated morphine withdrawal are largely diminished in the EphB1 KO mice.

NMDARs play important roles in neural plasticity and opiate-related alterations (Mao & Mayer, 2001; Nestler, 2001). NMDARs are heteromeric complexes containing both NR1 and NR2 subunits. They are located at the postsynaptic side of excitatory synapses, and are an important channel for $Ca^{2+}$ entry (Cull-Candy et al, 2001; Prybylowski & Wenthold, 2004). The NR1 subunit is widely distributed in the CNS, while the distribution of the NR2B subunit is more restricted, but includes the superficial layers of the DH (Boyce et al, 1999; Nagy et al, 2004). Re-introducing the deleted gene into specific brain regions by electroporation in NR2A KO mice showed that NR2A is important for morphine dependence and withdrawal (Inoue et al, 2003). Some evidence also points to opiate-induced increases in NR1 and NR2B protein levels as a contributor to morphine tolerance responses in the amygdale (Bajo et al, 2006). The present study provides the first evidence that chronic morphine exposure and/or withdrawal increases the p-NR2B subunit in the DH. Further, this increase of NR2B can be prevented and/or reduced by a blocking reagent for EphB receptors (FIG. 4). Ligand binding causes EphB receptor clustering and reciprocal phosphorylation on multiple tyrosine residues (Grunwald et al, 2004). The phosphorylated tyrosines recruit downstream signaling proteins containing SH2 domains, including Src family kinases such as Fyn (Grunwald et al, 2004; Murai & Pasquale, 2004). Fyn is physically associated with both the EphB receptors and NMDARs, and Fyn phosphorylates NR2B on tyrosines (Nakazawa et al, 2001). This might also occur in DH neurons following chronic morphine exposure and/or morphine withdrawal. Opiate systems interact with NMDARs such that activation of MOR results in $Ca^{2+}$ influx through the NMDAR ion-channel complex. The subsequent activation of various $Ca^{2+}$-dependent signaling pathways (Fan et al, 1999; Noda & Nabeshima, 2004) plays a central role in morphine dependence and withdrawal. The CaMKII protein can phosphorylate (activate) CREB, which leads to increases in c-Fos mRNA and c-Fos protein expression (Sheng et al, 1991). Gene expression is thought to play an important role in many forms of plasticity, including morphine dependence and withdrawal.

Trans-synaptic interactions between postsynaptic EphB receptors and presynaptic ephrinB are necessary for some forms of plasticity at mossy fiber synapses in the hippocampus (Contractor et al, 2002). It has recently been found that EphB receptors and their ephrinB ligands are upregulated pre-and postsynaptically at primary afferent synapses in the DH after nerve injury (Song et al, 2008a; Song et al, 2008b). The present results show that expression of the EphB receptor protein is also significantly increased following chronic morphine exposure and withdrawal (FIGS. 4A-4E). Surprisingly, expression of ephrinB1 and ephrinB2, and of proteins with phosphorylated tyrosines did not appear to be altered in the SC after morphine treatment and withdrawal (FIGS. 4F and 4G). In the absence of a corresponding alteration of its ephrinB ligands, how does clustering and reciprocal phosphorylation of the upregulated EphB receptors occur? One possibility is that the EphB receptors are directly modulated postsynaptically by signals such as NR2B, ERK (Nateri et al, 2007) and CREB (Ma et al, 2001; Watson & Latchman, 1995), or NO pathways (Muscoli et al, 2007; Pasternak, 2007) following chronic morphine treatment and/or morphine withdrawal. Interaction of EphB receptors with cAMP may also contribute to the postsynaptic effects of EphB receptors. For instance, expression of EphB2 is increased after exposure to forskolin, and a surge of cAMP can trigger transcriptional activity to augment expression of EphB2 receptor genes (Jassen et al, 2006).

Chronic morphine treatment induces an increase in CGRP in the terminals of primary afferent neurons, which accounts for the robust increase in CGRP immunoreactivity in DH (Trang et al, 2003). Although the underlying mechanism is unclear, the increase in CGRP may depend on activation of a MAPK pathway and phosphorylation of CREB (Ma et al, 2001), a transcription factor implicated in CGRP gene expression (Watson & Latchman, 1995). The present results show that the accumulation and depletion of CGRP in primary afferent terminals within the DH can be inhibited by an EphB receptor blocker. Such inhibition of CGRP may result from the blocker inhibiting the CREB signaling pathway (Ma et al, 2001; Watson & Latchman, 1995). Further studies are performed to show how the EphB receptors regulate expression of CGRP in presynaptic primary terminals following chronic morphine treatment.

In conclusion, the present study provides evidence for a novel mechanism contributing to opiate dependence and withdrawal symptoms, and a novel role for EphB receptor signaling in the development of morphine dependence and withdrawal. This study may also provide a potential pharmacological target for preventing, minimizing, or reversing morphine dependence, and thereby facilitate the use of opioid drugs in clinic. The clinical application may be extended to human beings with average body weight about 60 kg, which is about 1500 times of the average weight of mice (30-50 g) that were used in the study. Therapeutically effective dosage for clinical applications will be adjusted according to the body weight of the individual being treated.

While the invention has been shown in only a few of its forms, it should be apparent to those skilled in the art that it is not so limited but susceptible to various changes without departing from the scope of the invention.

What is claimed is:

1. A method for treating withdrawal symptoms due to opiate consumption, comprising: administering intrathecally to an individual in need of such treatment with a pharmaceutically effective amount of an EphB 1-Fc or EphB2-Fc blocking reagent.

2. The method of claim 1, wherein said EphB 1-Fc or EphB2-Fc blocking reagent is administered in an amount of from about 0.5 µg to about 75 mg.

3. The method of claim 2, wherein said EphB 1-Fc or EphB2-Fc blocking reagent is administered in an amount of from about 1µg to about 15 mg.

4. The method of claim 1, wherein said individual is a mammal.

5. The method of claim 4, wherein said mammal is human.

* * * * *